(12) United States Patent
Manova

(10) Patent No.: US 8,972,027 B2
(45) Date of Patent: Mar. 3, 2015

(54) IMPLANTABLE MEDICAL DEVICE INCLUDING ELECTRODE ELEMENT, ANCHORING ELEMENT AND ELASTIC ELEMENT

(71) Applicant: Shalom Manova, Savion (IL)

(72) Inventor: Shalom Manova, Savion (IL)

(*) Notice: Subject to any disclaimer, the term of this patent is extended or adjusted under 35 U.S.C. 154(b) by 0 days.

(21) Appl. No.: 13/726,465

(22) Filed: Dec. 24, 2012

(65) Prior Publication Data

US 2013/0116767 A1 May 9, 2013

Related U.S. Application Data

(63) Continuation-in-part of application No. PCT/IL2012/050190, filed on May 31, 2012.

(60) Provisional application No. 61/509,264, filed on Jul. 19, 2011.

(51) Int. Cl.
*A61N 1/05* (2006.01)

(52) U.S. Cl.
CPC .......... *A61N 1/059* (2013.01); *A61N 1/0587* (2013.01); *A61N 1/0573* (2013.01); *A61N 1/057* (2013.01); *A61N 1/0595* (2013.01)
USPC ........................ 607/130; 607/126; 607/131

(58) Field of Classification Search
CPC ... A61N 1/057; A61N 1/0573; A61N 1/0587; A61N 1/059
USPC .......................................... 607/126, 130, 131
See application file for complete search history.

(56) References Cited

U.S. PATENT DOCUMENTS

| 3,094,122 | A |   | 6/1963 | Gauthier et al. |   |
|---|---|---|---|---|---|
| 3,314,427 | A |   | 4/1967 | Stafford |   |
| 3,908,657 | A |   | 9/1975 | Kowarski |   |
| 4,149,535 | A |   | 4/1979 | Volder |   |
| 4,338,947 | A | * | 7/1982 | Williams | 600/374 |
| 4,341,226 | A |   | 7/1982 | Peters |   |
| 4,530,368 | A |   | 7/1985 | Saulson et al. |   |
| 4,633,880 | A |   | 1/1987 | Osypka et al. |   |
| 4,705,501 | A |   | 11/1987 | Wigness et al. |   |
| 5,350,419 | A |   | 9/1994 | Bendel et al. |   |
| 5,792,217 | A | * | 8/1998 | Camps et al. | 607/119 |
| 5,871,528 | A | * | 2/1999 | Camps et al. | 607/119 |
| 6,360,130 | B1 | * | 3/2002 | Duysens et al. | 607/132 |
| 7,949,411 | B1 | * | 5/2011 | Yang et al. | 607/122 |
| 8,255,062 | B2 | * | 8/2012 | Doan et al. | 607/116 |
| 2001/0029395 | A1 | * | 10/2001 | Stewart et al. | 607/116 |

(Continued)

FOREIGN PATENT DOCUMENTS

| DE | 3112762 A1 | 1/1983 |
|---|---|---|
| DE | 3401452 A1 | 8/1985 |

(Continued)

*Primary Examiner* — Niketa Patel
*Assistant Examiner* — Christopher A Flory
(74) *Attorney, Agent, or Firm* — Browdy and Neimark, PLLC

(57) ABSTRACT

A device comprising: a lead extending between a proximal end and a distal end, the lead comprising, at its distal end portion, an electrode element configured for fixing in a first body tissue, the lead further comprising: an anchoring element disposed between the proximal and the distal end for anchoring the device to a second tissue; and an elastic element disposed between the anchoring element and the distal end and configured so as to permit the pulling of the distal end away from the anchoring element against the biasing force of the elastic element.

19 Claims, 8 Drawing Sheets

(56) References Cited

U.S. PATENT DOCUMENTS

| | | | |
|---|---|---|---|
| 2004/0002665 A1* | 1/2004 | Parihar et al. | 600/587 |
| 2004/0102804 A1* | 5/2004 | Chin | 606/190 |
| 2006/0106442 A1* | 5/2006 | Richardson et al. | 607/119 |
| 2007/0213798 A1* | 9/2007 | Dreier et al. | 607/126 |
| 2007/0255295 A1 | 11/2007 | Starkebaum et al. | |
| 2007/0265611 A1* | 11/2007 | Ignagni et al. | 606/32 |
| 2008/0021505 A1 | 1/2008 | Hastings et al. | |
| 2008/0125828 A1* | 5/2008 | Ignagni et al. | 607/42 |
| 2008/0183257 A1* | 7/2008 | Imran et al. | 607/117 |
| 2008/0208248 A1* | 8/2008 | Rutten et al. | 606/205 |
| 2009/0138025 A1* | 5/2009 | Stahler et al. | 606/130 |
| 2009/0210041 A1 | 8/2009 | Kim et al. | |
| 2010/0016864 A1* | 1/2010 | Drake et al. | 606/129 |
| 2011/0092761 A1 | 4/2011 | Almog et al. | |
| 2011/0125163 A1* | 5/2011 | Rutten et al. | 606/108 |
| 2012/0190958 A1* | 7/2012 | Annest et al. | 600/375 |

FOREIGN PATENT DOCUMENTS

| | | |
|---|---|---|
| DE | 19959655 A1 | 6/2001 |
| EP | 0025704 A1 | 3/1981 |
| EP | 0234457 A2 | 9/1987 |
| EP | 0668087 A1 | 8/1995 |
| GR | 95100347 A | 5/1997 |
| WO | 9115153 A1 | 10/1991 |
| WO | 9503849 A1 | 2/1995 |
| WO | 0164282 A1 | 9/2001 |

* cited by examiner

IMPLANTABLE MEDICAL DEVICE INCLUDING ELECTRODE ELEMENT, ANCHORING ELEMENT AND ELASTIC ELEMENT

CROSS REFERENCE TO RELATED APPLICATIONS

This application is a continuation in part of international application number PCT/IL2012/050190 which claims the benefit of U.S. provisional patent application No. 61/509,264 filed on Jul. 19, 2011, both of which are hereby incorporated by reference herein.

FIELD

The present disclosure relates generally to a medical device, and more particularly to an implantable medical device that includes a lead for temporary electric stimulating (e.g. pacing), cardiac monitoring and/or other medical applications.

BACKGROUND

Temporary pacing of the heart, for instance after open-heart surgery, has been found to be effective in the treatment of postoperative cardiac arrhythmias which arise, for example, as a result of damage or injury to the conduction system during the surgery, hypothermia, preoperative anti-arrhythmia therapy (beta-blockers, calcium antagonists, digoxin) local edema, or temporary and intraoperative ischemia. In these cases, the heart's performance can show marked improvement when a relatively slow heart rate is elevated by electronic pacing. Patients who show postoperative sinus bradycardia can achieve improvements through AV sequential pacing.

For temporary pacing, one or more electrodes at the distal end of a lead are affixed to the heart, for instance to the epicardium or myocardium. Another electrode is attached to the outer skin surface or to the epicard or myocard as well. The distal end of the lead remains outside the body where electrical and mechanical connections to an external temporary pacemaker together with the skin electrode are made.

In the description herein, an element or end which is referred to as "proximal" is closer to a first tissue (e.g. closer to the heart or cardiac tissue) wherein an element or end which is referred to as "distal" is farther from a first tissue (e.g. farther from the heart or cardiac tissue).

A variety of methods have been used for embedding an electrode in the heart. One method utilizes a "zigzag" or helical shaped electrode. Prior to deployment, the zigzag or helical shaped electrode is rather compressed, but becomes spread out when pulled though the myocardium. Pacing electrodes of this kind are disclosed, for example, in U.S. Pat. No. 5,350,419 to Bendel et al. and U.S. Pat. No. 4,341,226 to Peters et al.

When pacing is no longer needed, or before the patient is discharged from the ward, the lead is detached from the heart by gently tugging on the external portion of the lead. The lead is then pulled out of the thorax and disposed of. Thus, on the one hand, the fixation of the lead to the heart must be stable enough to guarantee reliable heart pacing during the entire pacing period, and on the other hand, the fixation must not be too securely anchored in the heart so that it can be removed without injury upon tugging. Nonetheless, removal of an implanted lead entails a risk of damaging and/or rupturing the myocardium and/or a different part of the heart when the lead is pulled out. This can cause severe bleeding and/or cardiac tamponade, which can be a life threatening condition.

SUMMARY

In some embodiments, the present disclosure provides a device useful for electrically stimulating a tissue, monitoring an electrical signal from a tissue (herein, at times, the "first tissue" or "target tissue"), and/or another medical purpose. A non-limiting embodiment is for heart pacing post-cardiac surgery. In some embodiments, the device comprises a lead that is configured, inter-alia, for the provision of an electric link between a distal end at the body's exterior and an electrode at its proximal end portion that is embedded in or otherwise fixed to the target tissue. In distinction from known devices of this nature, that of some embodiments of the presently disclosed subject matter includes also an anchoring element and an elastic element disposed between the anchoring element and the distal end of the lead. Consequently, instead of pulling the distal end to disassociate the electrode from the tissue when the use of the device is exhausted, as is the case in known devices, in the device of some embodiments of the presently disclosed subject matter the anchoring element is used to anchor the lead to a second tissue that is other than the target tissue and when the use of the device is exhausted, the distal end is pulled away from the anchoring element against the elasticity of the elastic element, and once cut, the distal portion of the cut lead retracts back into the body. In embodiments relating to cardiac pacing, this eliminates injury to the cardiac tissue that often occurs in known pacing devices with a lead that extends from an electrode at its proximal end portion to the body's exterior.

In one aspect, in accordance with the presently disclosed subject matter, there is provided a device comprising a lead extending between a proximal end and a distal end, the lead comprising, at its proximal end portion, an electrode element configured for fixing in a first body tissue. The lead further comprises an anchoring element disposed between the proximal and the distal end for anchoring the device to a second tissue; and an elastic element disposed between the anchoring element and the distal end and configured so as to permit the pulling of the distal end away from the anchoring element against the biasing force of the elastic element.

In some embodiments of the device, the first tissue is the heart, myocardium or epicardium and the second tissue is the diaphragm.

In some embodiments of the device, the distal end is configured for connecting to monitoring or electric stimulating equipment, e.g. a heart pacing device.

In some embodiments of the device, a wire or cable included in the lead is insulated.

In some embodiments, the device further comprises a needle at its proximal end, proximal to the electrode element.

In some embodiments of the device, the electrode has a shape so as to increase zone of contact with the first tissue. In some of these embodiments, the electrode has a zigzag or helical shape.

In some embodiments, the device further comprises a needle at its distal end.

In some embodiments of the device, the elastic element is a helical spring or an element made of an elastic material.

In some embodiments of the device, the elastic element is fixed to a first point or section of a wire or cable included in the lead and to a second point or section of the wire or cable which is distanced from the first point by a first distance measured along the wire or cable that is longer than the length of the elastic element between the first point or section and second point or section in a relaxed state thereof.

In some embodiments of the device, the elastic element is a hollow element with a lumen that accommodates a portion of a wire or cable included in the lead and that can elastically deform from a first, resting state to a second, strained state in which it is biased to re-deform into the first state, the deformation from the first to the second state being induced by pulling the proximal end away from the anchoring element.

In some embodiments of the device, the elastic element is formed from a segment of a wire or cable included in the lead.

In some embodiments of the device, the anchoring element is constituted by a loop formed from a wire or cable included in the lead.

In some embodiments of the device, the anchoring element is an element attached to a wire or cable included in the lead.

In another aspect, in accordance with the presently disclosed subject matter, there is provided an implantable device comprising: a lead extending between a proximal end and a distal end, the lead comprising, at its proximal end portion, an electrode configured for fixing onto a subject's heart or into a cardiac tissue, a distal end of the lead being configured to be inserted through a chest wall and skin from interior to exterior, the lead further comprising: an anchoring element disposed between the proximal and the distal end for anchoring the device to the patient's diaphragm, and an elastic element disposed between the anchoring element and the distal end and configured so as to permit the pulling of the distal end away from the anchoring element against the biasing force of the elastic element.

In another aspect, in accordance with the presently disclosed subject matter there is provided a cardiac pacemaker system comprising one or more devices, each device comprising a lead extending between a proximal end and a distal end, the lead comprising, at its proximal end portion, an electrode element configured for fixing in a first body tissue, the lead further comprising: an anchoring element disposed between the proximal and the distal end for anchoring the device to a second tissue; and an elastic element disposed between the anchoring element and the distal end and configured so as to permit the pulling of the distal end away from the anchoring element against the biasing force of the elastic element.

In another aspect, in accordance with the presently disclosed subject matter there is provided cardiac pacemaker system comprising one or more implantable devices, each device comprising a lead extending between a proximal end and a distal end, the lead comprising, at its proximal end portion, an electrode configured for fixing onto a subject's heart or into a cardiac tissue, a distal end of the lead being configured to be inserted through a chest wall and skin from interior to exterior, the lead further comprising: an anchoring element disposed between the proximal and the distal end for anchoring the device to the patient's diaphragm, and an elastic element disposed between the anchoring element and the distal end and configured so as to permit the pulling of the distal end away from the anchoring element against the biasing force of the elastic element.

In another aspect, in accordance with the presently disclosed subject matter there is provided a method of implanting a device that comprises a lead extending between a proximal end and a distal end, the lead comprising an elastic element, an electrode element between a proximal end of the lead and the elastic element, and an anchoring element between the electrode element and the elastic element, the method comprising: securing the electrode element to a first tissue; fixing the anchoring element to a second tissue; and inserting the distal end of the lead through a body wall and skin from interior to exterior.

In some embodiments, the method further comprises: pulling a distal end of the lead away from the skin surface, thereby causing the elastic element to be in a stretched state; and cutting the lead above the skin surface to leave a cut portion extending into the body, and releasing the lead to enable the biasing force of the elastic element to cause it to revert to a relaxed contracted state, and consequently retract the cut portion into the body.

BRIEF DESCRIPTION OF THE DRAWINGS

In order to understand the currently disclosed subject matter and to see how it may be carried out in practice, embodiments will now be described, by way of non-limiting example only, with reference to the accompanying drawings, in which.

Figure 1:
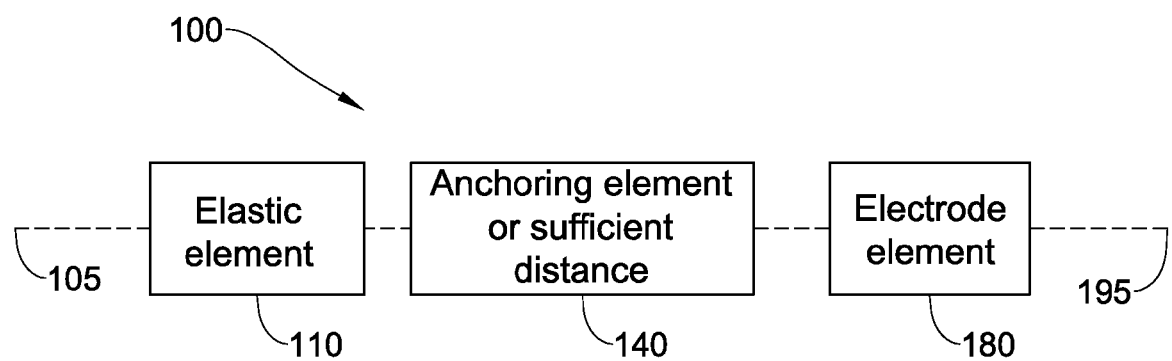
FIG. 1 shows a device comprising a lead, in accordance with some embodiments of the presently disclosed subject matter.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate identical or analogous elements.

DETAILED DESCRIPTION OF SOME EMBODIMENTS

In the following detailed description, numerous specific details are set forth in order to provide a thorough understanding of the subject matter. However, it will be understood by those skilled in the art that some embodiments of the subject matter may be practiced without these specific details. In other instances, well-known methods, stages, features, structures, characteristics and/or elements have not been described in detail so as not to obscure the subject matter.

Usage in the specification of the term "such as", "e.g.", "possibly", "it is possible", "optionally", "say", "one embodiment", "embodiments", "an embodiment", "some embodiments", "various embodiments", "other embodiments", "another embodiment", "for example" "one example", "an example" "some examples", "examples", "another example", "various examples", "other examples", "for instance", "an instance", "one instance", "some instances", "another instance", "other instances", "various instances" "one case", "cases", "some cases", "another case", "other cases", "various cases", or variants thereof means that a particular described method, stage, feature, structure, characteristic, or element is included in at least one non-limiting embodiment of the subject matter, but not necessarily included in all embodiments. The appearance of the same term does not necessarily refer to the same embodiment(s).

It should be appreciated that certain methods, stages, features, structures, characteristics and/or elements disclosed herein, which are, for clarity, described in the context of separate embodiments, may also be provided in combination in a single embodiment. Conversely, various features, structures and/or characteristics disclosed herein, which are, for brevity, described in the context of a single embodiment, may also be provided separately or in any suitable sub-combination.

Embodiments of the presently disclosed subject matter relate to a device. In some embodiments, the device may comprise a lead. The lead may comprise an elastic element, an electrode element at a proximal end of the lead or between a proximal end of the lead and the elastic element, and an anchoring element, or sufficient distance to allow for later addition of an anchoring element, between the elastic element and the electrode element. More particularly, the device in some of these embodiments may comprise a lead extending between a proximal end and a distal end, the lead comprising, at its proximal end portion, an electrode element configured for fixing in a first body tissue, the lead further comprising: an anchoring element disposed between the proximal and the distal end for anchoring the device to a second tissue; and an elastic element disposed between the anchoring element and the distal end and configured so as to permit the pulling of the distal end away from the anchoring element against the biasing force of the elastic element. When it is stated that the electrode element is at the proximal end portion of the lead, this means that the electrode element may be at the proximal end, but not necessarily. For instance, the electrode element may alternatively be anywhere between the proximal end and the anchoring element or anywhere between the proximal end and the future location of the anchoring element which will be added later.

For simplicity of description, it is assumed that the proximal end of the device corresponds to the proximal end of the lead comprised in the device, and that the distal end of the device corresponds to the distal end of the lead comprised in the device.

As used herein, an elastic element is an element which has the property of elasticity (up to an elastic limit). Therefore an elastic element deforms from a relaxed contracted state (also referred to as relaxed state or resting state, or any variant thereof) to a stretched state (also referred to as strained state or any variant thereof) when a pulling force is applied to the elastic element. This pulling force is against the biasing force (also referred to as restoring force or any variant thereof) exerted by the elastic element. When in the stretched state the elastic element is biased to re-deform (also referred to as revert or any variant thereof) into the relaxed state so that when the pulling force is no longer applied, the elastic element reverts to the relaxed contracted state due to the biasing force exerted by the elastic element. In some embodiments, the maximum biasing force which would restore the elastic element to the relaxed contracted state is limited so that retraction of the exposed portion of the lead into the body (described below) does not cause internal injury. For instance, if under Hooke's law the biasing force $F=-kx$ where k is a constant and x is a displacement, the value of k and/or of x may be limited so that the biasing force is also limited. However, in other embodiments, there may not be a limit on the maximum biasing force, for instance if the device is implanted in a way which minimizes the likelihood that such a retraction would cause internal injury.

The disclosure does not limit the type of elastic element. An elastic element may be for example, a coiled (also referred to as helical or any variant thereof) spring, an element made of an elastic material (e.g. elastic fiber or cable), etc.

The disclosure also does not limit the amount that an elastic element may be stretched. However for the purpose of illustration only, one example is now provided. In this example, the lead may be lengthened between the proximal and distal ends by up to 2-3 cm when included elastic element(s) is/are stretched from a relaxed contracted state. However in other examples, the lead may be lengthened by a larger or smaller amount.

The disclosure also does not limit the type of electrode element. In some embodiments, an electrode element may have a shape which increases the zone of contact with the first tissue. For instance, an electrode element may have a zigzag or helical shape. In other embodiments, an electrode element may not have such a shape.

The disclosure also does not limit the type of anchoring element. Depending on the embodiment, the device may be initially manufactured with or without an anchoring element. Therefore after the initial manufacturing of the device, an anchoring element may not necessarily be present, as long as an anchoring element is present when the device is being implanted into a body. If the device excludes an anchoring element when originally manufactured, the device should be configured in a manner which allows for an anchoring element to be added at a later time. For instance the device may be manufactured in a manner that ensures that there will be sufficient distance between an elastic element and an electrode element to later add an anchoring element. This "sufficient" distance may be equivalent to the sum of the desired distance between an elastic element and an anchoring element and the desired distance between the anchoring element and an electrode element, or may be a larger distance than the sum of the desired distances. For instance, the distance may be larger if a segment of a wire or cable included in the lead which connects between the elastic element and the electrode element will later be used to form the anchoring element, as in some embodiments described below.

The disclosure also does not limit the distances between the various elements included in the device, and depending on the embodiment there may be any suitable distances between the various elements. However, for the purpose of illustration only, one example of possible distances is now provided. In this example, there is a distance of about 6 cm between a distal end of the lead and an elastic element, a distance of about 3-5 cm between an elastic element and an anchoring element, and a distance of about 5-10 cm between an anchoring element and an electrode element. However in other examples, each of these distances may be larger or smaller.

Optionally the lead may also comprise one or more other elements, of the same type (e.g. additional electrode element(s), additional elastic element(s), additional anchoring element(s)). and/or of different type(s) (e.g. needle(s), wire(s), cable(s), etc), between the distal and proximal ends of the lead.

For instance, there may possibly be a needle, e.g. a circular needle, at the proximal end of the lead, proximal to an electrode element, and possibly a needle, for instance a straight pointed needle, at the distal end of the lead, which may be included in the device that is being implanted, having been added during the initial manufacturing of the device or at a later time.

With regard to any wire(s) and/or cable(s) which may be included in the lead, each of which may run at least part of the way between the distal and proximal ends of the lead, the anchoring, elastic and/or electrode elements mentioned above may be fixed (i.e. attached) to such a wire or cable, and/or such a wire or cable may be formed into one or more of these elements. For instance, an elastic element may be fixed to a wire or cable, or for instance a segment of a wire or cable may be formed into an elastic element. An anchoring element, for instance, may be attached to a wire or cable, or for instance a segment of a wire or cable may be formed into an anchoring element. An electrode element, for instance, may be attached to a wire or cable, or for instance a segment of a wire or cable may be formed into an electrode element. Continuing with describing the instance of the electrode element, and assuming that a wire or cable included in the lead is an insulated wire or cable with the insulation made, for instance from a biocompatible material, such as polyethylene, and with the diameter of the insulated wire or cable being e.g. around 0.45 mm, the electrode element may or may not be formed from an uninsulated segment of the wire or cable More details on these instances are provided below.

For the purpose of illustration only, the device is described below with respect to a cardiac application, where the first tissue is the heart or a cardiac tissue (e.g. epicardium or myocardium) and the second tissue is non-cardiac tissue. However, it should be evident to the reader, that the device may be used for other applications, where the first tissue is not the heart or a cardiac tissue, with similar description to what is disclosed below, mutatis mutandis.

In a cardiac application, during implantation of the device, an electrode element included in the lead is fixed onto a patient's (i.e. subject's) heart or into a cardiac tissue e.g. in the epicardium or myocardium. An anchoring element is anchored to a non-cardiac tissue, for instance to the diaphragm, and the distal end of the lead is inserted through the chest wall and skin from the interior to the exterior, for instance in order to be connected to monitoring equipment, electric stimulating equipment (e.g. pacemaker, also known as heart pacing device) or any other medical equipment.

When the device is no longer needed, the exposed distal end of the lead is pulled away from the skin surface on the chest wall, causing the elastic element to be stretched. The elastic element permits the pulling of the distal end away from the anchoring element against the biasing force of the elastic element. However, due to the anchoring element, little or no pulling force is applied to the electrode element as a consequence. The lead is cut above the skin surface, for example with a pair of scissors. Cutting the lead causes the elastic element to spontaneously revert to a contracted state. This causes the exposed (distal) portion of the lead to retract into the body through the skin and chest wall. The truncated lead may remain in the body, and the electrode element does not need to be detached from the heart, unless it is desired to do so.

A medical system may comprise one or more of the devices and optionally other element(s) such as any medical equipment to which the device(s) is/are capable of being connected, etc. For example, a cardiac pacemaker system may comprise one or more of the devices. Optionally, the cardiac pacemaker system may also comprise other element(s) such as a pacemaker (i.e. heart pacing device), any other electric stimulating equipment, etc. A monitoring system, for example, may comprise one or more of the devices. Optionally, the monitoring system may also comprise other element(s) such as monitoring equipment, etc.

Referring now to the drawings, FIG. 1 shows a device comprising a lead 100, in accordance with some embodiments of the presently disclosed subject matter. In order to simplify illustration, lead 100 is shown as including a single elastic element 110 and a single electrode element 180 between a distal end 105 and a proximal end 195, but in some embodiments lead 100 may include a plurality of elastic elements and/or electrode elements. Additionally, for simplicity of illustration, lead 100 is shown as including, between elastic element 110 and electrode element 180 a single anchoring element or sufficient distance 140 to allow for later addition of an anchoring element. In some embodiments, however, there may be a plurality of anchoring elements or sufficient distance to allow the later addition of a plurality of anchoring elements. Elastic element 110, anchoring element/sufficient distance 140, and electrode element 180 are shown connected by a dotted line in FIG. 1 so as to indicate that these elements are located between distal end 105 and proximal end 195 of lead 100 in the order shown, namely electrode element 180 at proximal end 195 or between proximal end 195 and elastic element 110, and anchoring element/sufficient distance 140 between elastic element 110 and electrode element 180. Optionally, lead 100 may include one or more other elements, as discussed above.

Figure 2A:
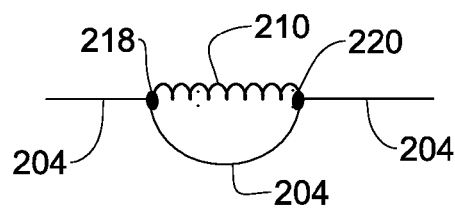
FIG. 2A shows an elastic element in a relaxed contracted state, in accordance with some embodiments of the presently disclosed subject matter.
Figure 2B:
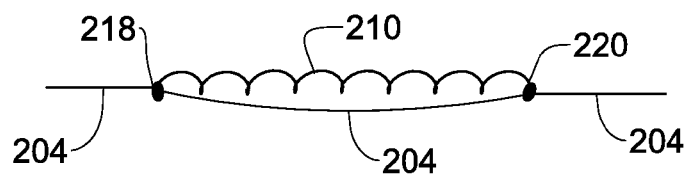
FIG. 2B shows the elastic element of FIG. 2A in a stretched state, in accordance with some embodiments of the presently disclosed subject matter.

FIG. 2A shows an example of an elastic element 210 in a relaxed contracted state, in accordance with some embodiments of the presently disclosed subject matter. Elastic element 210 is an example of elastic element 110 shown in FIG. 1. As shown in FIG. 2A, elastic element 210 is a coiled spring which is attached to a wire or cable 204 included in lead 100 at a first point or section 218 of wire or cable 204, and at a second point or section 220 of wire or cable 204. Wire or cable 204 continues beyond elastic element 210 in both directions, proximally and distally, although not necessarily all the way between proximal end 195 and distal ends 105. Although the ends of elastic element 210 are shown attached to wire or cable 204, it is possible that in some embodiments a different point or section than an end on elastic element 210 is alternatively attached. First and second points or sections 218 and 220 of wire or cable 204 are distanced from each other by a distance measured along the wire or cable that is longer than the length of elastic element 210 between points/sections 218 and 220 when elastic element 210 is in a relaxed state. Therefore, wire or cable 204 is shown bulging out around elastic element 210 between points/sections 218 and 220 when the elastic element is in a relaxed contracted state. In embodiments where the ends of elastic element 210 are attached. first and second points or sections 218 and 220 of wire or cable 204 are distanced from each other by a distance measured along wire or cable 204 that is longer than the distance between the two ends of elastic element 210 in a relaxed state. FIG. 2B shows elastic element 210 of FIG. 2A in a stretched state, in accordance with some embodiments of the presently disclosed subject matter.

Figure 3A:
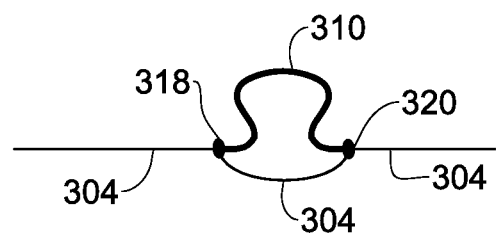
FIG. 3A shows an elastic element in a relaxed contracted state, in accordance with some embodiments of the presently disclosed subject matter.
Figure 3B:
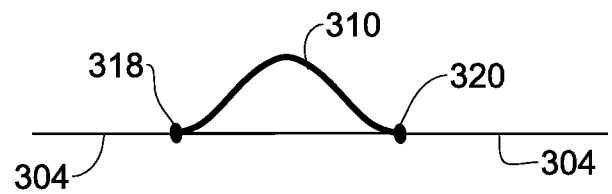
FIG. 3B shows the elastic element of FIG. 3A in a stretched state, in accordance with some embodiments of the presently disclosed subject matter.

FIG. 3A shows another example of an elastic element 310 in a relaxed contracted state, in accordance with some embodiments of the presently disclosed subject matter. Elastic element 310 is an example of elastic element 110 shown in FIG. 1. As shown in FIG. 3A, elastic element 310 is in the shape of an omega shape, U shape, or any other appropriate shape. Elastic element 310 may or may not be hollow. Elastic element 310 is attached to a wire or cable 304 of lead 100 at a first point or section 318 of wire or cable 304, and at a second point or section 320 of wire or cable 304. Wire or cable 304 continues beyond elastic element 310 in both directions, proximally and distally although not necessarily all the way between proximal end 195 and distal ends 105. Although the ends of the elastic element 310 are shown attached to wire or cable 304, it is possible that in some embodiments a different point or section than an end on elastic element 310 is alternatively attached. First and second points or sections 318 and 320 of wire or cable 304 are distanced from each other by a distance measured along wire or cable 304 that is longer than the length of elastic element 310 between points/sections 318 and 320 when elastic element 310 is in a relaxed state. Therefore, wire or cable 304 is shown bulging out around elastic element 310 between points/sections 318 and 320 when the elastic element is in a relaxed contracted state. In embodiments where the ends of elastic element 310 are attached, first and second points or sections 318 and 320 of wire or cable 304 are distanced from each other by a distance measured along the wire or cable that is longer than the distance between the two ends of elastic element 310 in a relaxed state. FIG. 3B shows elastic element 310 of FIG. 3A in a stretched state, in accordance with some embodiments of the presently disclosed subject matter.

Figure 4A:
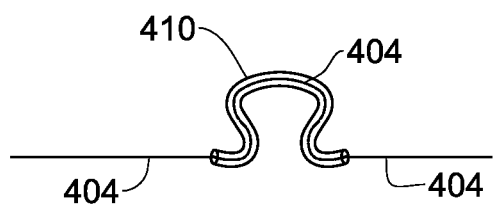
FIG. 4A shows an elastic element in a relaxed contracted state, in accordance with some embodiments of the presently disclosed subject matter.
Figure 4B:
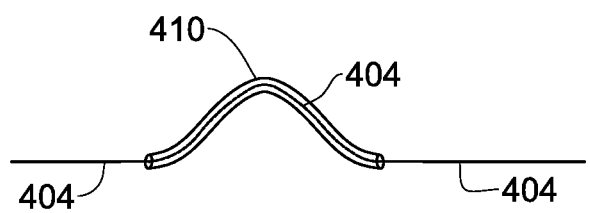
FIG. 4B shows the elastic element of FIG. 4A in a stretched state, in accordance with some embodiments of the presently disclosed subject matter.

FIG. 4A shows another example of an elastic element 410 in a relaxed contracted state, in accordance with some embodiments of the presently disclosed subject matter. Elastic element 410 is an example of elastic element 110 shown in FIG. 1. As shown in FIG. 4A, elastic element 410 is in the shape of an omega shape, U shape, or any other appropriate shape. Elastic element 410 is hollow and a lumen of elastic element 410 accommodates a portion of a wire or cable 404 included in lead 100. Wire or cable 404 continues beyond elastic element 410 in both directions, proximally and distally although not necessarily all the way between proximal end 195 and distal ends 105. In some of these embodiments, elastic element 410 may be attached to wire or cable 404 at a first point or section of wire or cable 404, and at a second point or section of wire or cable 404, however in other embodiments attachment may not be necessary. FIG. 4B shows elastic element 410 of FIG. 4A in a stretched state, in accordance with some embodiments of the presently disclosed subject matter.

Figure 5A:
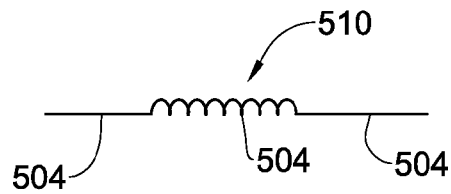
FIG. 5A shows an elastic element in a relaxed contracted state, in accordance with some embodiments of the presently disclosed subject matter.
Figure 5B:
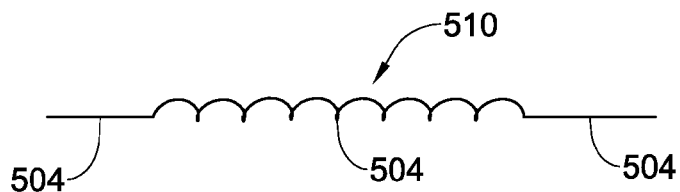
FIG. 5B shows the elastic element of FIG. 5A in a stretched state, in accordance with some embodiments of the presently disclosed subject matter.

FIG. 5A shows another example of an elastic element 510 in a relaxed contracted state, in accordance with some embodiments of the presently disclosed subject matter. Elastic element 510 is an example of elastic element 110 shown in FIG. 1. As shown in FIG. 5A, elastic element 510 is formed from a segment of wire or cable 504 included in lead 100 by coiling the segment of wire or cable 504. Wire or cable 504 continues beyond the elastic element in both directions, proximally and distally although not necessarily all the way between proximal end 195 and distal ends 105. In some other examples, elastic element 510 may be formed from a segment of wire or cable 504 in any other appropriate way. FIG. 5B shows elastic element 510 of FIG. 5A in a stretched state, in accordance with some embodiments of the presently disclosed subject matter.

The examples shown in FIGS. 2A, 2B, 2C, 2D, 3A, 3B, 4A, 4B, 5A, 5B are provided for the purpose of illustration only, and any type of (elastic) element which has the property of elasticity may be used in lead 100. As mentioned above, depending on the embodiment lead 100 may include one or more elastic elements. In some embodiments with a plurality of elastic elements, the elastic elements may all be of the same type, or the elastic elements may be of two or more different types. For instance, the type or types of elastic elements may include any of the examples of elastic elements illustrated in FIGS. 2A, 2B, 2C, 2D, 3A, 3B, 4A, 4B, 5A, 5B and/or may include any other example(s). In embodiments with a plurality of elastic elements the configuration of the elastic elements with respect to one another may be of any suitable configuration. For instance the configuration may include serial elastic elements and/or parallel elastic elements, but this is not necessarily so.

Figure 6A:
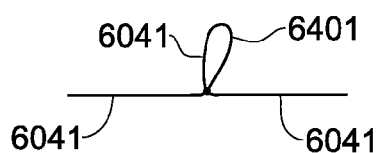
FIG. 6A shows an anchoring element, in accordance with some embodiments of the presently disclosed subject matter.

FIG. 6A shows an example of an anchoring element 6401, in accordance with some embodiments of the presently disclosed subject matter. Anchoring element 6401 is an example of anchoring element 140 shown in FIG. 1. As shown in FIG. 6A, anchoring element 6401 is constituted by a loop formed from a wire or cable 6041 included in lead 100 (e.g. by creating a fixed loop in wire or cable 6041). Wire or cable 6041 continues beyond anchoring element 6401 in both directions, distally and proximally, and therefore at least runs part of the way between elastic element 110 and electrode element 180.

Figure 6B:
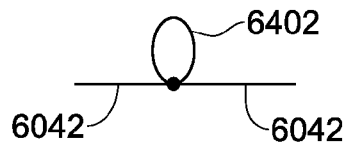
FIG. 6B shows an anchoring element, in accordance with some embodiments of the presently disclosed subject matter.

FIG. 6B shows an example of an anchoring element 6402, in accordance with some embodiments of the present disclosed subject matter. Anchoring element 6402 is an example of anchoring element 140 shown in FIG. 1. As shown in FIG. 6B, anchoring element 6402 is an element in the form of a loop which is attached to one point on a wire or cable 6042 included in lead 100, or is attached to a section of wire or cable 6042 included in lead 100. Wire or cable 6042 continues beyond anchoring element 6402 in both directions, distally and proximally, and therefore at least runs part of the way between elastic element 110 and electrode element 180.

Figure 6C:
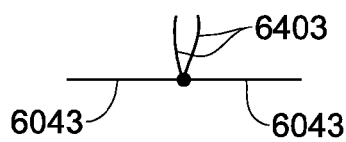
FIG. 6C shows an anchoring element, in accordance with some embodiments of the presently disclosed subject matter.

FIG. 6C shows an example of an anchoring element 6403, in accordance with some embodiments of the presently disclosed subject matter. Anchoring element 6403 is an example of anchoring element 140 shown in FIG. 1. As shown in FIG. 6C, anchoring element 6403, which is an element that is not in the form of a loop, is attached to one point on a wire or cable 6043 included in lead 100, or is attached to a section of wire or cable 6043 included in lead 100. Anchoring element 6403 may include one or more pieces. Wire or cable 6043 continues beyond anchoring element 6403 in both directions, distally and proximally, and therefore at least runs part of the way between elastic element 110 and electrode 180.

Figure 6D:
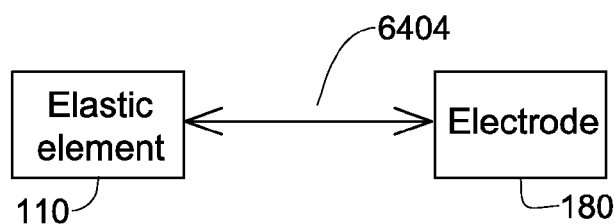
FIG. 6D shows an example where there is sufficient distance between an elastic element and an electrode element to allow for later addition of an anchoring element, in accordance with some embodiments of the presently disclosed subject matter.

FIG. 6D shows an example where there is sufficient distance 6404 between elastic element 110 and electrode element 180 of lead 100 to allow for later addition of an anchoring element, in accordance with some embodiments of the presently disclosed subject matter. Sufficient distance 6404 is an example of sufficient distance 140 shown in FIG. 1. An anchoring element which may be added later may be an anchoring element as illustrated in FIG. 6A, 6B, 6C or any other suitable anchoring element. For instance, assume that an anchoring element which will be added later will be formed from a wire or cable included in lead 100 which at least runs part of the way between elastic element 110 and electrode element 180. In this instance, "sufficient" distance which would allow such a loop to be formed may equal e.g. the sum of the amount of wire or cable which will be used for forming the loop, the desired distance between the loop and elastic element 110, and the desired distance between the loop and electrode 180 element, or may be higher.

The examples shown in FIGS. 6A, 6B, 6C, are provided for the purpose of illustration only, and any type of anchoring element may be used which enables the firm fixation of a point or section of lead 100 between elastic element 110 and electrode element 180, so that when a pulling force is applied to distal end 105 of lead 100 and assuming the fixation is maintained, little or no pulling force is experienced by any element of lead 100 (e.g. electrode element 180) proximal from the fixed point or section. As mentioned above, depending on the embodiment, lead 100 may include one or more anchoring elements and/or sufficient distance to allow for the later addition of one or more anchoring elements. In some embodiments with a plurality of anchoring elements, the anchoring elements may all be of the same type, or the anchoring elements may be of two or more different types. For instance, the type or types of anchoring elements may include any of the examples of anchoring elements illustrated in FIGS. 6A, 6B, 6C, and/or may include any other example(s). In embodiments with a plurality of anchoring elements the configuration of the anchoring elements with respect to one another may be of any suitable configuration. For instance the configuration may include serial anchoring elements and/or parallel anchoring elements, but this is not necessarily so.

For ease of illustration and description, embodiments of a device comprising a lead 2 are illustrated in FIGS. 7, 8, 9A, 9B, 10A, 10B. Lead 2 is an example of lead 100 shown in FIG. 1. Lead 2 has an elastic element 16 in accordance with embodiments illustrated in FIGS. 2A and 2B, and an anchoring element 15 in accordance with embodiments illustrated in FIG. 6A, and therefore elastic element 16 is an example of elastic element 110 (FIG. 1) and anchoring element 15 is an example of anchoring element/sufficient distance 140 (FIG. 1). However, it should be evident to the reader that these figures could have illustrated different embodiments of lead 100 which additionally or alternatively included any other example of elastic element(s), any other example of anchoring element(s), and/or sufficient distance to add anchoring element(s), for instance as in any of the examples described above.

Figure 7:
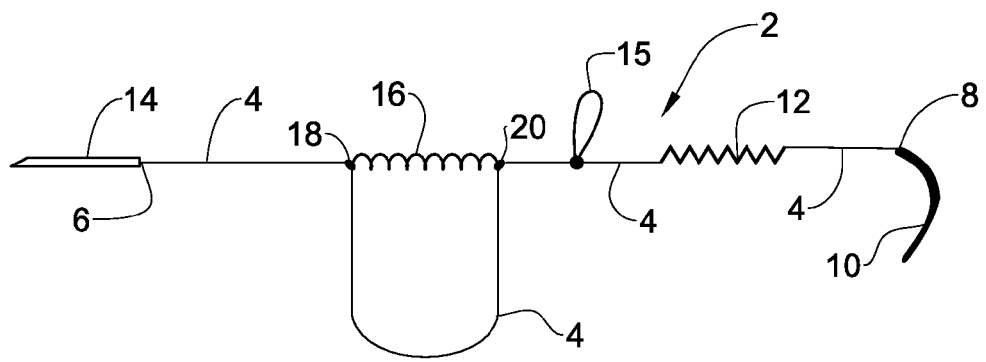
FIG. 7 shows a device comprising a lead having an elastic element in accordance with some embodiments of the presently disclosed subject matter, the elastic element being shown in a contracted relaxed state.
Figure 8:
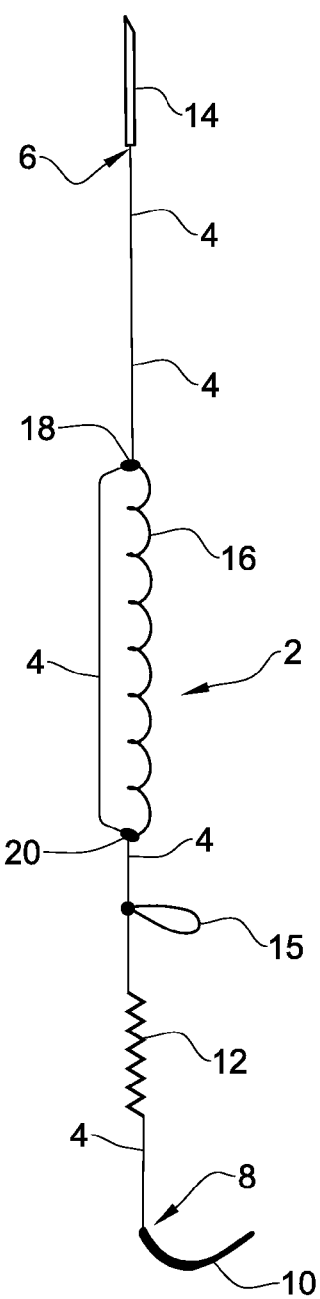
FIG. 8 shows the device with the elastic element in a stretched state, in accordance with some embodiments of the presently disclosed subject matter.

FIGS. 7 and 8 show a device comprising lead 2 in accordance with some embodiments of the presently disclosed subject matter. Lead 2 comprises an insulated wire or cable 4 having a distal end 6 and a proximal end 8. Distal end 6 of wire or cable 4 is an example of distal end 105 of lead 100 and proximal end 8 of wire or cable 4 is an example of proximal end 195 of lead 100 (see FIG. 1). The insulation of wire or cable 4 may be made for example from a biocompatible material, such as polyethylene. The diameter of the insulated wire or cable may be, for example, around 0.45 mm. Attached to proximal end 8 of wire or cable 4 is a curved suture needle 10. Adjacent to proximal end 8 is an electrode 12 which is formed from an uninsulated segment of wire or cable 4. Electrode 12 is an example of electrode element 180 (FIG. 1) and is configured to be fixed (i.e. embedded) in a first tissue such as the heart or a cardiac tissue (e.g. myocardial or epicardial tissue). In the embodiments shown in FIGS. 7 and 8, electrode 12 is a "zigzag" or helical shaped electrode, as is known in the art. Wire or cable 4 terminates at its distal end 6 in a straight pointed needle 14.

Lead 2 further comprises elastic element 16 that may be for example, a coiled spring or an elastic fiber or cable. Elastic element 16 is attached to wire or cable 4 at a first point 18 of wire or cable 4, and at a second point 20 of wire or cable 4. In FIG. 7, elastic element 16 is shown in its relaxed, contracted configuration. It is assumed that the ends of elastic element 16 are attached to first and second points 18 and 20. First and second points 18 and 20 are distanced from each other by a distance measured along wire or cable 4 that is longer than the distance between the two ends of elastic element 16 in the relaxed contracted state. Therefore wire or cable 4 is shown bulging out around the elastic element 16 between the points 18 and 20 when elastic element 16 is in the relaxed contracted state. In FIG. 8, elastic element 16 is shown after having been stretched. Between elastic element 16 and electrode 12 is anchoring element 15 that may be formed, for example, by creating a fixed loop in wire or cable 4. The anchoring element is for anchoring the device to a second tissue such as a non-cardiac tissue (e.g. a diaphragm 17)

Figure 9A:
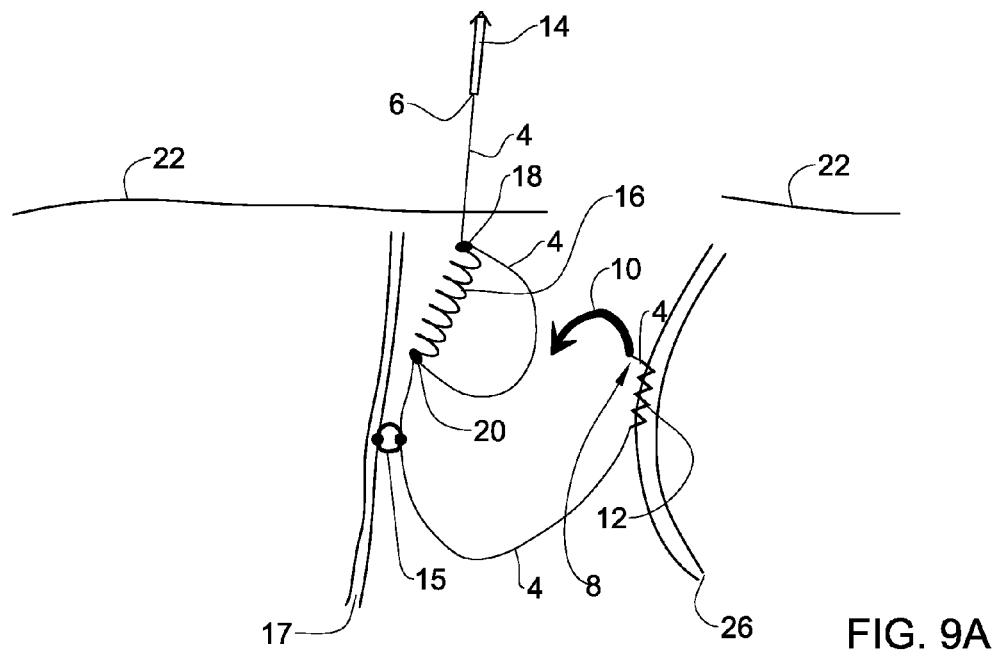
FIG. 9A shows implantation of the device of FIGS. 7 and 8, in accordance with some embodiments of the presently disclosed subject matter.

FIG. 9A shows implantation of the device comprising lead 2, in accordance with some embodiments of the presently disclosed subject matter. In FIG. 9A, the curved suture needle 10 has been looped through the epicardium or myocardium 26 with elastic element 16 in its contracted state shown in FIG. 7. Electrode 12 is fixed in the heart or into a cardiac tissue, for example in the epicardium or myocardium 26 of the right ventricle or right atrium. Anchoring element 15 has been sutured to a non-cardiac tissue such as diaphragm 17. Straight needle 14 has been inserted through the chest wall 22 and skin from the interior to the exterior. Preferably between electrode 12 and anchoring element 15, wire or cable 4 is not tensioned, so that no pulling force is applied by wire or cable 4 to epicardium or myocardium 26. The suturing of anchoring element 15 to diaphragm 17 is sufficiently secure so that anchoring element 15 remains anchored to diaphragm 17 even if a pulling force of reasonable proportion or less is applied to distal end 6. Reasonable proportion may vary depending on the embodiment. For instance a pulling force of reasonable proportion may be equal to or larger than the pulling force expected when distal end 6 is pulled away from the skin surface as described below with reference to FIG. 9B.

Figure 9B:
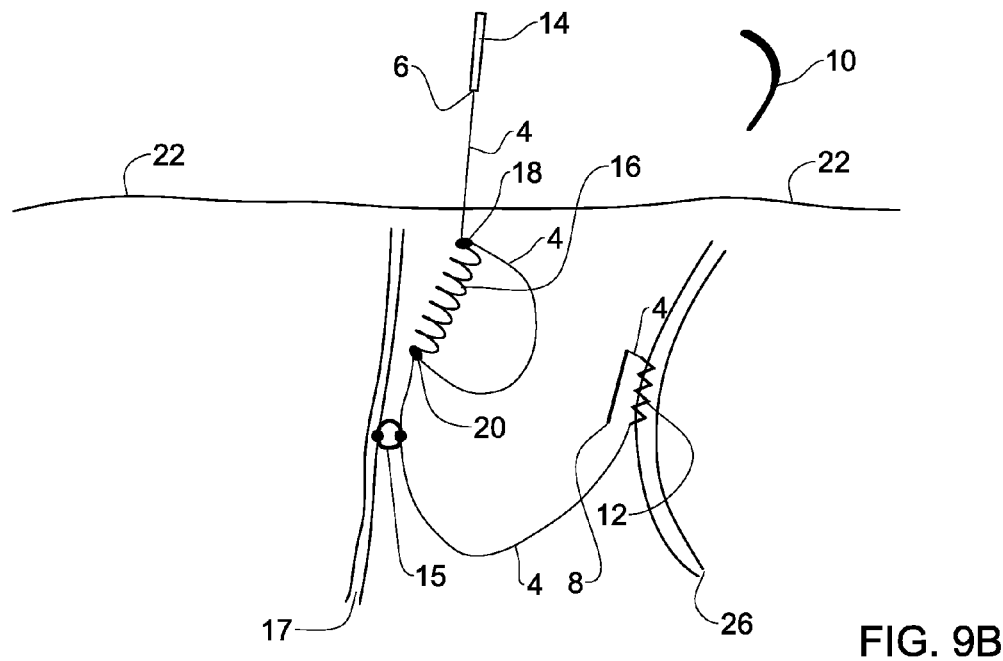
FIG. 9B shows the device of FIGS. 7 and 8 after completion of the implantation, in accordance with some embodiments of the presently disclosed subject matter.

FIG. 9B shows the device after completion of the implantation, in accordance with some embodiments of the presently disclosed subject matter. Curved suture needle 10 was cut off from wire or cable 4 prior to closing the chest wall 22. The tip of the straight needle 14 has also been cut off to produce a straight blunt probe which can be connected to monitoring equipment, electric stimulating equipment (e.g. pacemaker), or any other medical equipment (not shown).

As mentioned above, a medical system may be considered to comprise one or more of the devices described herein. Optionally the medical system may also comprise other element(s), for instance any medical equipment (e.g. monitoring, electric stimulating, or any other medical equipment) to which the device(s) is/are capable of being connected, etc.

Figure 10A:
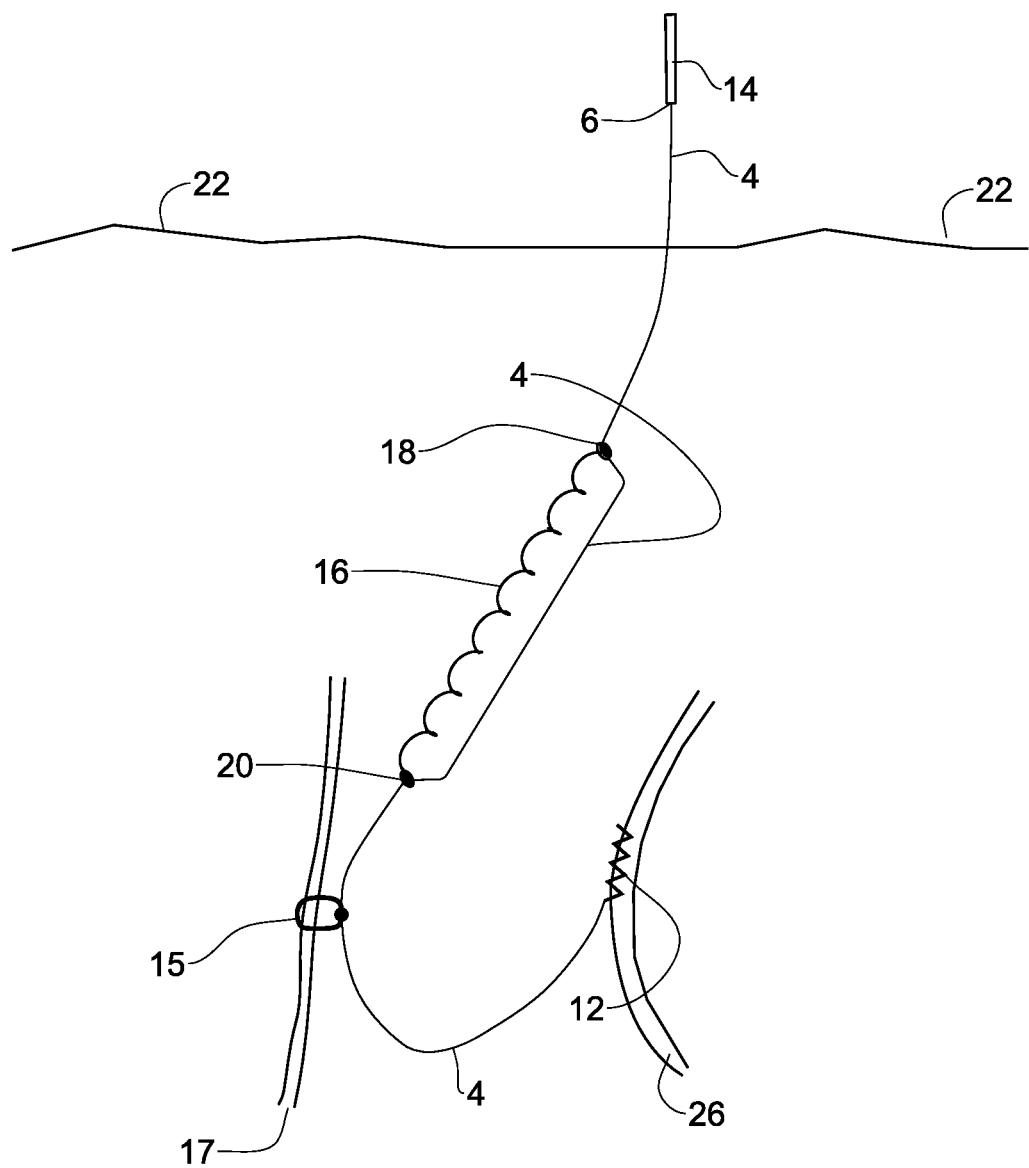
FIG. 10A shows stretching of the elastic element in the implanted device, in accordance with some embodiments of the presently disclosed subject matter.
Figure 10B:
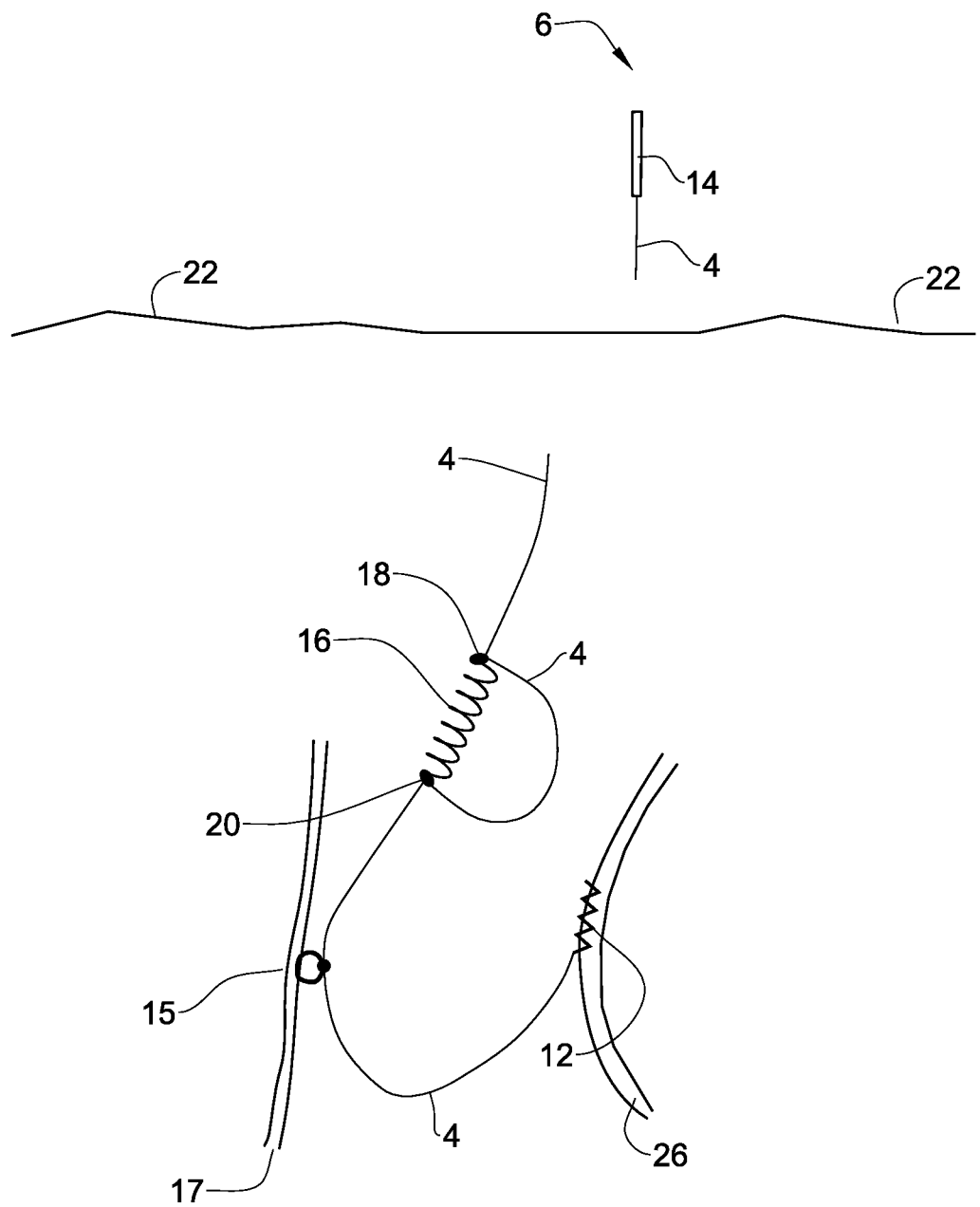
FIG. 10B shows retraction of the exposed portion of the lead into the body after cutting off the end of the lead, in accordance with some embodiments of the presently disclosed subject matter.

Refer now to FIG. 10A which shows the stretching of elastic element 16 in the implanted device, and to FIG. 10B which shows retraction of the exposed portion of the lead into the body after cutting off the end of the lead, in accordance with some embodiments of the presently disclosed subject matter.

Referring first to FIG. 10A, when the device is no longer needed, distal end 6 of wire or cable 4 can be disconnected from the electric stimulating equipment, monitoring equipment, or any other medical equipment to which it was connected. Distal end 6 of the wire or cable 4 is then pulled away from the skin surface on chest wall 22. This causes elastic element 16 to be stretched, as shown in FIG. 10A. Elastic element 16 permits the pulling of distal end 6 away from anchoring element 15 against the biasing force of elastic element 16. However, because of the anchoring of anchoring element 15 to diaphragm 17, the pulling on distal end 6 and the stretching of elastic element 16 results in little or no pulling force on epicardium or myocardium 26. Then, as shown in FIG. 10B, wire or cable 4 is cut above the skin surface, for example, with a pair of scissors. Cutting wire or cable 4 causes elastic element 16 to spontaneously revert to its contracted configuration. This causes the exposed (distal) portion of the cut end of wire or cable 4 to be retracted into the body through the skin and chest wall 22. The truncated lead can remain in the body, if desired, thus avoiding the need to detach electrode 12 from epicardium or myocardium 26.

Figure 11:
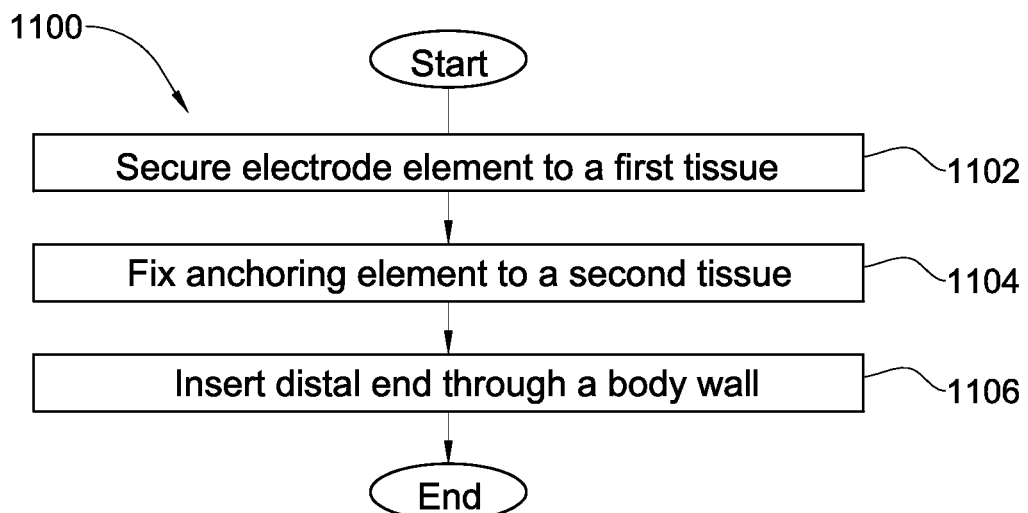
FIG. 11 is a flowchart of a method of implanting a device, in accordance with some embodiments of the presently disclosed subject matter.

FIG. 11 is a flowchart of a method 1100 of implanting a device, in accordance with some embodiments of the presently disclosed subject matter.

It is assumed that the device provided for implantation comprises lead 100 for which some embodiments are described herein.

In stage 1102, electrode element 180 is secured to a first tissue. Assuming a cardiac application, the first tissue may be, for example, the heart or a cardiac tissue such as the epicardium or myocardium of a patient. For instance a needle such as a curved suture needle attached to a proximal end of lead 100 may be used for suturing distal end 195 of lead 100 to a first tissue.

In stage 1104, anchoring element 140 is fixed to a second tissue. Again assuming a cardiac application, the second tissue may be non-cardiac tissue, such as the diaphragm of the patient. For instance, a needle, such as one not attached to lead 100, may be used for suturing anchoring element 140 to the second tissue.

Alternatively, stages 1102 and 1104 may be reversed.

In stage 1106, distal end 105 of lead 100 is inserted through a body wall (e.g. a chest wall) and skin of the patient from interior to exterior. For instance, a needle such as a straight needle attached at a proximal end of lead 100 may be used for inserting.

Optionally, if there was a needle at proximal end 195 of lead 100, the needle may be cut away prior to closing the wall of the patient. Optionally, if there was a needle at distal end 105 of lead 100, the tip of the needle may be cut off to produce a straight blunt probe which may be connected to a pacemaker or other medical equipment.

Figure 12:
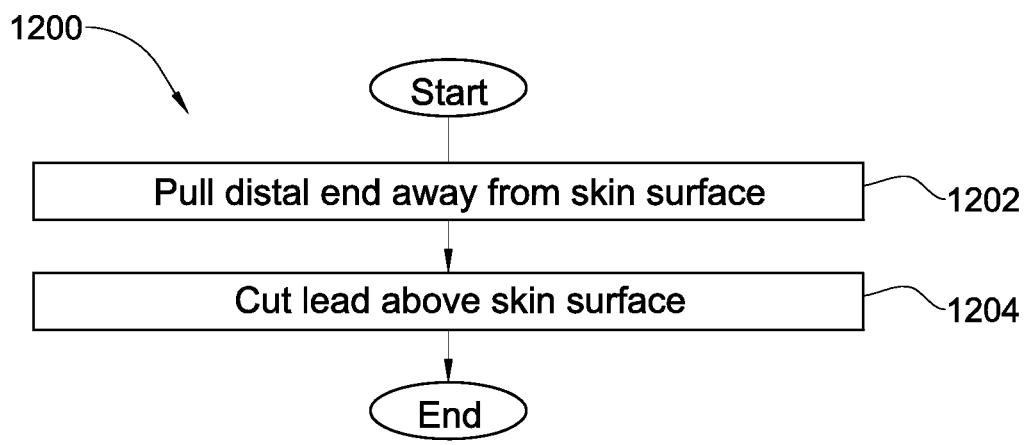
FIG. 12 is a flowchart of a method performed after an implanted device is no longer needed, in accordance with some embodiments of the presently disclosed subject matter.

FIG. 12 is a flowchart of a method 1200 performed after an implanted device is no longer needed, in accordance with some embodiments of the presently disclosed subject matter. It is assumed that the device comprises lead 100 for which some embodiments are described herein.

In stage 1202, distal end 105 of lead 100 is pulled away from the skin surface, thereby causing elastic element 110 of lead 100 to be in a stretched state. However, due to the anchoring by anchoring element 140, little or no pulling force is exerted on the first tissue as a consequence.

In stage 1204 lead 100 is cut above the skin surface to leave a cut portion extending into the body. Lead 100 is released by way of the cutting or otherwise. The releasing of lead 100 enables the biasing force of elastic element 110 to cause elastic element 110 to revert to a relaxed contracted state, and consequently retract the cut portion of lead 100 into the body.

It is noted that the disclosure does not impose a limitation on the amount that elastic element 110 is stretched in stage 1202 nor on the amount of lead 100 which is cut in stage 1204. However in some embodiments the exposed portion of lead 100, after the cutting, should not be more than the difference between the length of lead 100 after elastic element 110 was stretched in stage 1202, and the length of lead 100 before the stretching (i.e. when elastic element 110 was in a relaxed contracted state before stage 1202), so that the exposed portion of cut lead 100 retracts into the body.

The truncated lead which remains in the body after stage 1206, does not need to be removed from the body of the patient, unless it is desired to do so.

Figure 13:
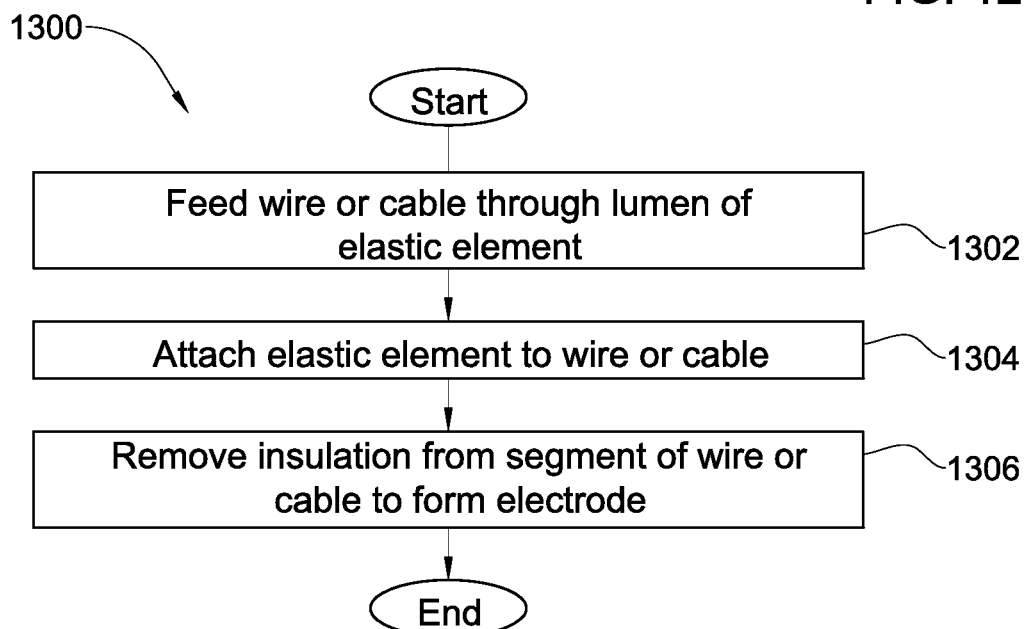
FIG. 13 is a flowchart of a method of manufacturing a device, in accordance with some embodiments of the presently disclosed subject matter.

FIG. 13 is a flowchart of a method 1300 of manufacturing a device comprising a lead, in accordance with some embodiments of the presently disclosed subject matter. It is assumed that the lead is lead 100 for which some embodiments are described herein.

In optional stage 1302, a wire or cable, for instance which is insulated, is fed through a lumen of a hollow elastic element, for instance elastic element 410 illustrated in FIGS. 4A and 4B.

In optional stage 1304, two points or sections of elastic element 110 (e.g. two ends) are attached to two points or sections on the wire or cable. The attachment may use any procedure such as cold or hot welding, tying, infusion (i.e. casting), glue, any combination of the above, etc. The elastic element may for instance be the elastic element illustrated in any of FIGS. 2A, 2B, 3A, 3B, 4A, 4B.

It is noted that for an elastic element such as the elastic element illustrated in FIGS. 5A and 5B, neither stages 1302 nor 1304 are performed but instead during manufacturing a wire or cable may be formed into an elastic element, for instance by coiling.

Stage 1304 may or may not be optional for an elastic element such as elastic element 410 illustrated in FIGS. 4A and 4B.

The order of stages 1304 and 1306, when both performed, may alternatively be reversed.

In optional stage 1306, the insulation is removed from a segment of the wire or cable at proximal end 195 of lead 100, or between elastic element 110 and proximal end 195 of lead 100, so as to form electrode element 180. Electrode element, 18—for instance may be at a sufficient distance proximally from elastic element 110 to allow for anchoring element 140. (It is noted that anchoring element 140 may have been previously included in lead 100 during manufacturing method 1300, or may be added to lead 100 later in manufacturing method 1300 or after the manufacturing method 1300 has been completed).

In some embodiments, stage 1306 may be performed earlier on in method 1300, for instance before stage 1302 or 1304 rather than in the order illustrated in FIG. 13. In some embodiments, stage 1306 may be omitted, for instance if electrode element 180 is not formed by removing insulation from a segment of the wire or cable.

Optionally manufacturing method 1300 may include any of the following procedures: attaching electrode(s), forming and/or attaching anchoring element(s), and/or attaching needle(s), etc. Depending on the embodiment, any of these procedures may be performed before or after any of stages 1302, 1304, and/or 1306.

Optionally manufacturing method 1300 may include performing stage 1302, 1304 and/or 1306 for additional elastic element(s) and/or electrode element(s), and/or may include forming additional elastic element(s) and/or electrode(s) from wire(s) and/or cable(s) of the lead.

In embodiments where manufacturing method 1300 includes attaching anchoring element(s) 140 to wire(s) and/or cable(s), any anchoring element 140 may be made up of any material which is strong enough to allow anchoring element 140 to remain intact when a pulling force of reasonable proportion or less is applied to distal end 105 of lead 100. Any anchoring element 140 may be attached to a wire or cable included in lead 100 using any suitable attaching method so that anchoring element 140 remains attached even if a pulling force of reasonable proportion or less is applied to distal end 105 of lead 100. For instance, the attaching method may include tying, gluing, hot and/or cold welding, any combination of the above, or any other method which would allow anchoring element 140 to remain attached to the wire or cable even if a pulling force of reasonable proportion or less is applied to distal end 105 of lead 100. Reasonable proportion may vary depending on the embodiment. For instance a pulling force of reasonable proportion may be equal to or larger than the pulling force expected when distal end 105 of lead 100 is pulled away from the skin surface such as in stage 1202 of method 1200 discussed above.

Alternatively to any of methods 1100, 1200 and 1300 discussed above, in some embodiments a method of implanting a device, a method performed after an implanted device is no longer needed, and/or a method of manufacturing a device may include fewer, more and/or different stages than those discussed herein.

While the presently disclosed subject matter has been shown and described with respect to particular embodiments, it is not thus limited. Numerous modifications, changes and improvements within the scope of the presently disclosed subject matter will now occur to the reader.

The invention claimed is:

1. A device comprising:
a lead extending between a proximal end and a distal end, the lead comprising, at a proximal end portion thereof, an electrode element configured for fixing in a first body tissue, the lead further comprising: an anchoring element disposed between the proximal end and the distal end for anchoring the device to a second tissue; and an elastic element disposed between the anchoring element and the distal end and configured so as to permit the pulling of the distal end away from the anchoring element against the biasing force of the elastic element while stretching said elastic element without displacing said electrode element.

2. The device of claim 1, wherein the first tissue is a heart, myocardium or epicardium and the second tissue is a diaphragm.

3. The device of claim 1, wherein the distal end is configured for connecting to monitoring or electric stimulating equipment.

4. The device of claim 1, wherein a wire or cable included in the lead is insulated.

5. The device of claim 1, further comprising a needle at its proximal end, proximal to said electrode element.

6. The device of claim 1, wherein the electrode has a shape so as to increase a zone of contact with the first tissue.

7. The device of claim 6, wherein the electrode has a zigzag or helical shape.

8. The device of claim 1, further comprising a needle at its distal end.

9. The device of claim 1, wherein the elastic element is a helical spring or an element made of an elastic material.

10. The device of claim 1, wherein the elastic element is fixed to a first point or section of a wire or cable included in the lead and to a second point or section of the wire or cable which is distanced from the first point by a distance measured along the wire or cable that is longer than the length of the elastic element between the first point or section and second point or section in a relaxed state thereof.

11. The device of claim 1, wherein the elastic element is a hollow element with a lumen that accommodates a portion of a wire or cable included in the lead and that can elastically deform from a first, resting state to a second, strained state in which it is biased to re-deform into the first state, the deformation from the first to the second state being induced by pulling the distal end away from the anchoring element.

12. The device of claim 1, wherein the elastic element is formed from a segment of a wire or cable included in the lead.

13. The device of claim 1, wherein the anchoring element is constituted by a loop formed from a wire or cable included in the lead.

14. The device of claim 1, wherein the anchoring element is an element attached to a wire or cable included in the lead.

15. The device of claim 1, wherein:
said device is an implantable device; the distal end of said lead is configured to be inserted through a chest wall and skin from interior to exterior; and the second tissue is the patient's diaphragm.

16. An implantable device comprising:
a lead extending between a proximal end and a distal end, the lead comprising, at its proximal end, an electrode configured for fixing onto a subject's heart or into a cardiac tissue, the distal end of said lead being configured to be inserted through a chest wall and skin from interior to exterior, the lead further comprising: an anchoring element disposed between the proximal and the distal end for anchoring the device to the patient's diaphragm, and an elastic element disposed between the anchoring element and the distal end and configured so as to permit the pulling of the distal end away from the anchoring element against the biasing force of the elastic element while stretching said elastic element without displacing said electrode.

17. A cardiac pacemaker system comprising one or more devices, each device comprising a lead extending between a proximal end and a distal end, the lead comprising, at a proximal end portion thereof, an electrode element configured for fixing in a first body tissue, the lead further comprising: an anchoring element disposed between the proximal end and the distal end for anchoring the device to a second tissue; and an elastic element disposed between the anchoring element and the distal end and configured so as to permit the pulling of the distal end away from the anchoring element against the biasing force of the elastic element while stretching said elastic element without displacing said electrode.

18. The device of claim 17, wherein:
said device is an implantable device; the distal end of said lead is configured to be inserted through a chest wall and skin from interior to exterior; and the second tissue is the patient's diaphragm.

19. A cardiac pacemaker system comprising one or more implantable devices, each device comprising a lead extending between a proximal end and a distal end, the lead comprising, at its proximal end, an electrode configured for fixing onto a subject's heart or into a cardiac tissue, the distal end of said lead being configured to be inserted through a chest wall and skin from interior to exterior, the lead further comprising: an anchoring element disposed between the proximal and the distal end for anchoring the device to the patient's diaphragm, and an elastic element disposed between the anchoring element and the distal end and configured so as to permit the pulling of the distal end away from the anchoring element against the biasing force of the elastic element while stretching said elastic element without displacing said electrode.

* * * * *